United States Patent [19]
Stüber et al.

[11] Patent Number: 5,457,114
[45] Date of Patent: Oct. 10, 1995

[54] AMIDINOPHENYLALANINE DERIVATIVES, A PROCESS FOR THE PREPARATION THEREOF, USE THEREOF AND AGENTS CONTAINING THESE AS ANTICOAGULANTS

[75] Inventors: Werner Stüber, Lahntal; Gerhard Dickneite, Marburg; Rainer Koschinsky, Kirchhain; Cenek Kolar, Marburg, all of Germany

[73] Assignee: Behringwerke Aktiengesellschaft, Marburg, Germany

[21] Appl. No.: 190,682

[22] Filed: Jan. 25, 1994

Related U.S. Application Data

[63] Continuation of Ser. No. 879,360, May 7, 1992, abandoned.

[30] Foreign Application Priority Data

May 11, 1991 [DE] Germany .................. 41 15 468.1

[51] Int. Cl.$^6$ .................. A61K 37/02; C07K 5/06
[52] U.S. Cl. .................. 514/319; 514/210; 514/212; 514/326; 514/330; 514/381; 514/382; 514/419; 514/456; 514/603; 540/200; 540/453; 540/607; 546/205; 546/226; 546/22; 548/253; 548/540; 549/398; 564/86
[58] Field of Search .................. 540/200, 483, 540/607; 546/226, 205, 22; 548/540, 253; 564/86; 549/398; 514/210, 212, 319, 326, 330, 381, 382, 419, 456, 603

[56] References Cited

U.S. PATENT DOCUMENTS

| | | | |
|---|---|---|---|
| 4,537,896 | 8/1985 | Claesson | 546/206 |
| 4,791,102 | 12/1988 | Bernat | 546/226 |

FOREIGN PATENT DOCUMENTS

| | | | |
|---|---|---|---|
| 236164 | 9/1987 | European Pat. Off. | |
| 236163 | 9/1987 | European Pat. Off. | |
| 155954 | 7/1982 | Germany | A61K 31/16 |
| 235866 | 5/1986 | Germany | C07C 143/72 |

OTHER PUBLICATIONS

Wilbraham et al "Organic and Biological Chemistry" Benjamin/Cummings Publishing, 1984, pp. 222–225.
J. Stuerzebecher et al. "Synthetische Inhibitoren der Serinproteinasen," *Pharmazie*, 42, 1987, pp. 114–121.
D. Horn et al., "Synthese van Nα–(8–Chinolonsulfonyl)–4–amidinophenylalaninamiden Thrombininhibitoren," *Pharmazie*, 40, 1985, pp. 615–616.
Synthesis of 2–Amino–3–Boronopropionic Acid: A Boron–containing Analogoue of Aspartic Acid, D. H. Kinder et al., J. Orig. Chem. (1987), 52, pp. 2352–2454.
The Synthesis And Structure of some N–(L–aspart–4–oyl)–β–D–xylopyranosylamine Derivatives, Rita Walczyna and Janusz Sokolowski, Carbohydrate Research, 180 (1988) pp. 147–151.
Synthesis Of Glycosylmides And 4–N–Glycosyl–L–Asparagine Derivatives, Anatoly Ya. Khorlin et al., Carbohydrate Research, 85 (1980) pp. 201–208.
Eine Einfache Synthese Von N–Acyl–Glykosylaminen, Almuth Klemer and Michael Kohla, J. Carbohydrate Chemistry, 7(4) (1988) pp. 785–797.
Synthesis The α and β anomer of An N–triglycosyl Dipeptide, T. Takeda et al., Carbohydrate Research, 201, (1990), pp. 71–79.
Solid–Phase Synthesis Of Gylcopeptides: Synthesis Of N$^α$Fluorenylmethoxycarbonyl L–Asparagine Nβ– Glycosides, Laszlo Urge et al., Tetrahedron Letters, vol. 32, No. 29 (1991) pp. 3445–3448.
Selective Inhibition Of Thrombin By (2R,4R)–4–Methyl–1 –[N$^2$–[(3–methyl–1,2,3, 4–tetrahydro–8–quinolinyl)sulfonyl]–L–arginyl)] –2–piperdinecarboxylic Acid, Ryoji Kikumoto et al., Biochemistry vol. 23, No. 1 (1984) pp. 85–90.
Anticoagulant Therapy With MD805 Of A Hemodialysis Patient With Heparin–Induced Thrombocytopenia, T. Matsuo et al., Thrombosis Research 58, 1990, pp. 663–666. pp. 1201–1210.
Pharmacological Characterization Of A New Highly Effective Synthetic Thrombin Inhibitor, B. Kaiser et al., Biomed. Biochim. Acta 44, (1985) 7/8, pp. 1201–1210.
Pharmacological Characterization Of A New Structural Variant of 4–Amidinophenylalanine Amide–type Synthetic Trombin Inhibitor, J. Hauptmann et al., Pharmazie 44 (1989) pp. 282–284.

*Primary Examiner*—Ceila Chang
*Attorney, Agent, or Firm*—Finnegan, Henderson, Farabow, Garrett & Dunner

[57] ABSTRACT

Amidinophenylalanine derivatives of the formula I

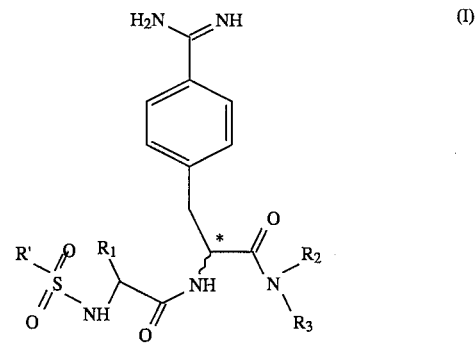

the synthesis of these compounds, the use thereof and pharmaceutical agents which contain these compounds are described.

14 Claims, No Drawings

AMIDINOPHENYLALANINE DERIVATIVES, A PROCESS FOR THE PREPARATION THEREOF, USE THEREOF AND AGENTS CONTAINING THESE AS ANTICOAGULANTS

This application is a continuation of application Ser. No. 07/879,360, filed May 7, 1992, now abandoned.

The invention relates to amidinophenylalanine derivatives, to the synthesis of these compounds, to the use thereof and to pharmaceutical agents which contain these compounds.

It is known that a number of pathophysiological conditions result in consumption of antithrombin III (AT III), the principal thrombin inhibitor in the plasma. A decrease in AT III results in an increased risk of thrombosis, and is also found, inter alia, in cases of inborn AT III deficiency. A decrease to values below 75% of normal results in thromboembolic complications. These complications often occur in the form of disseminated intravascular coagulation after surgery and in states of shock. In many cases this is associated with the occurrence of life-threatening blood clots. Employed to date in medicine for the therapy and prophylaxis of thrombotic disorders are anticoagulants with various modes of action. The substances employed for acute counteraction of a risk of thrombosis are, for example, AT III, heparin and, recently, also hirudin. Long-term prophylaxis is also carried out with coumarin and indanedione derivatives. However, the stated anticoagulants are, in some cases, associated with considerable disadvantages.

For example, only parenteral administration is possible for heparin because of its polysaccharide structure, and its effect is also dependent on a functioning antithrombin III level. Coumarins directly counteract protein biosynthesis, in that the vitamin K-dependent coagulation factors II, VII, IX and X can no longer be made available in sufficient quantity, and thus the coagulation potential is reduced. This results in the efficacy having a time lag. Known side effects are hemorrhagic dermal necroses, nausea and hair loss.

By contrast, low molecular weight thrombin inhibitors have the advantage that they act, independently of cofactors, directly on thrombin by binding directly to the active center and thus blocking the enzyme, as it were. The chemical structure of these substances means that they have the potential for oral administration.

Particularly well known are amino-acid derivatives based on arginine and based on amidinophenylalanine. The first group includes compounds such as D-phenylalanyl-L-prolylargininaldehyde and (2R,4R)-4-methyl-1-[$N^2$-(3-methyl-1,2,3,4-tetrahydro-8-quinolinesulfonyl)-L-arginyl]-2-piperidinecarboxylic acid monohydrate ("MD 805"). MD 805 is a competitive specific thrombin inhibitor which is also employed in therapy. Another known amidinophenylalanine derivative is beta-naphthylsulfonyl-glycyl-R,S-4-amidinophenylalanyl piperidide (NAPAP). Derivatives of NAPAP are described in EP 0236 163 and EP 0236 164. In these, glycine ($NH_2$—$CH_2$—COOH) has been replaced by another amino acid of the structure $NH_2$—$CHR_1$—COOH in which $R_1$ is a lower alkyl group, a lower hydroxyalkyl group, a phenyl group or a 4-hydroxyphenyl group. 4-Amidinophenylalanine (Aph) can be methylated to give N-methyl-Aph.

In addition, various derivatizations of NAPAP on the arylsulfonyl, "bridge" glycine and on the piperidine ring have been described. The most suitable according to this are alpha- or beta-naphthylsulfonyl groups at the N terminus, whereas heteroarylsulfonyl groups such as 8-quinolinesulfonyl are worse by powers of ten. Another disadvantage of these compounds, which particularly relates to the NAPAP structures, is that their tolerability is low, the pharmacokinetic behavior is unfavorable, and in some cases the specificity is too low, in which respect particular mention should be made of excessive antitrypsin activity. Oral administration of substances which contain para-amidinophenylalanine is impeded by the fact that the stability to intestinal enzymes and liver enzymes is not optimal so that the substances are too rapidly metabolized in the intestine and in the liver. It is possible by replacing the piperidine in NAPAP by a proline to improve the tolerability and achieve more favorable pharmakokinetics. However, a very crucial disadvantage of the proline compound is an unwanted loss of the thrombin inhibitory action by a factor of 100 compared with NAPAP. Furthermore, there is as yet no possibility of significantly improving the specificity of these compounds for thrombin and trypsin by introducing substituents.

The object of the invention was therefore to provide novel compounds which are based on amidinophenylalanine and which are superior to the known compounds on the basis of their antithrombotic activity and have a high enzymatic resistance, an improved tolerability, an improved specificity and improved pharmacokinetics.

This invention accordingly relates to compounds of the formula I

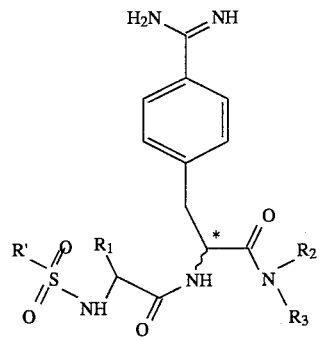

in which

R' is a naphthalene ring which is bonded in the alpha or beta position and is optionally derivatized with alkyl groups which contain up to 3 carbon atoms, and/or alkoxy groups each with up to 3 carbon atoms, or is a tetralin ring or indane ring which is bonded in the alpha or beta position and is optionally derivatized with alkyl groups which are composed of up to 3 carbon atoms, and/or also alkoxy groups each with up to 3 carbon atoms, or is a phenyl ring which is optionally derivatized with alkyl groups which contain up to 4 carbon atoms, and/or with up to three groups of the structure O—X in which O is oxygen and X is hydrogen, methyl, ethyl, n-propyl, i-propyl or tert.-butyl, and/or with a group of the structure —COOY in which Y is hydrogen, methyl, ethyl, n-propyl, i-propyl, tert.-butyl, i-butyl, i-pentyl or neo-pentyl, or is a chroman system which is preferably derivatized with up to 5 alkyl groups which contain up to 3 carbon atoms, $R_1$ is a group of the structure A—B with A=$(CH_2)_n$— and n=1–4 and B is an acid functionality selected from the group comprising carboxyl functionality which optionally can be esterified or is in amide form, the esters containing an alcohol with up to 17 carbon atoms, sulfonic acid functionality, a functionality of an acid of phosphorus, a boronic acid functionality and tetrazole group, or $R_1$ is a group of the structure A—B—C where A has the above meaning, B is carbonyl or sulfonyl, and the group C is derived from an N-bonded alpha, beta, gamma or delta amino acid or from the group of N-glycosidically linked uronic acids, and $R_2$ and $R_3$ can be identical or different and are alkyl groups with up to 4 carbon atoms or together form a heterocyclic ring which has up to 8 ring members and which can be derivatized with a hydroxyl group or a hydroxyalkyl group with up to 3 carbon atoms, and this hydroxyl group is optionally in esterified form, the corresponding acids being carboxylic acids which contain up to 17 carbon atoms, and in which the carbon atom marked with * is in the R or S structure, but preferably in the R structure.

These novel compounds have the feature that the amino acid $R_1$ in formula I is an acidic amino acid. Examples of acidic amino acids are the amino acids, which occur in proteins, glutamic acid and aspartic acid or else cysteic acid, but also unnatural amino acids such as aminoadipic acid or 3-phosphonoalanine or 2-amino-3-boropropionic acid. Since, as a consequence of an asymmetrically substituted carbon atom, these amino acids are chiral substances, the novel compounds prepared using these amino acids also show different activity, it being mainly the corresponding amino acids in the L form which result in final compounds with higher activity.

The group A specified in the structure $R_1$ is preferably such than n assumes the number 1 or 2, and the number 1 is very particularly preferred. If the group C is an amino acid, this preferably means an alpha, beta, gamma or delta-amino acid. Examples of such amino acids are alpha-aminoadipic acid, alpha-aminobutyric acid, gamma-aminobutyric acid, 4-aminobenzoic acid, 2-aminobenzoic acid, epsilon-aminocaproic acid, 1-aminocyclohexanecarboxylic acid, 2-aminocyclohexanecarboxylic acid, 3-aminocyclohexanecarboxylic acid, 4-aminocyclohexanecarboxylic acid, 1-aminocyclopentanecarboxylic acid, 2-amino-4,5-dimethyl- 3-phenoxazone-1,8-dicarboxylic acid, 2-amino-3-hydroxy- 4-methylbenzoic acid, alpha-amino-isobutyric acid, aminohydroxybutyric acid, β-aminoisobutyric acid, alanine, β-alanine, dehydroalanine, C-allylglycine, alliin, 2-amino-3-methylbutyl-1,3-thiazoline-5-carboxylic acid, 6-aminopenicillanic acid, alpha-aminopimelic acid, 1-aminocyclopropanecarboxylic acid, asparagine, aspartic acid, alpha-aminosuberic acid, azetidinecarboxylic acid, aziridinecarboxylic acid, baikiaine, C-benzylphenylalanine, canavanine, citrulline, cysteine, cystathionine, djenkolic acid, 3,4-dihydroxyphenylalanine, 4-sulfonylphenylalanine, 2,2-dimethyl-1,3-thiazolidine-4-carboxylic acid, felinine, glutamine, glutamic acid, glycine, hexahydronicotinic acid, homocysteine, histidine, homoserine, delta-hydroxylysine, gamma-hydroxyproline, β-hydroxyproline, isoleucine, isoserine, isovaline, kynorenine, lanthionine, leucenine, leucine, lysergic acid, methionine, mimosine, minaline, norleucine, norvaline, pantonine, pipecolic acid, penicillamine, phenylalanine, C-phenylglycine, picolinic acid, proline, dehydroproline, β-phenylserine, 2-pyridylalanine, 5-pyrrolidone-2-carboxylic acid, 3-pyrazolylalanine, quinoxaline-2-carboxylic acid, roseonine, sarcosine, selenocysteine, selenomethionine, serine, statine, 1,3-thiazol-2-ylalanine, β-(1,3-thiazol-2-yl)alanine, threonine, thyronine, thyroxine, 1,3-thiazoline-2-carboxylic acid, tertiaryleucine, tryptophan, tryptathionine, tyrosine, valine. These amino acids may, in the case where they are optically active, be in the D or L form.

In the case where C is an amidino dicarboxylic acid, which includes, for example, D- or L-glutamic acid or aspartic acid, one of these carboxyl groups can be derivatized, and the alpha carboxyl group is preferably derivatized. Derivatives of this type are preferably amides derived, for example, from ammonia, methylamine, dimethylamine, benzylamine, piperidine or morpholine.

If the group C is a N-glycosidically linked uronic acid, a compound of this type can be represented by the following formula:

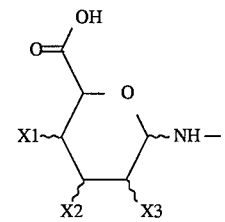

with

X1=—H, —OH, —$CH_3$, O-acetyl,

X2=—H, —OH, —$CH_3$, O-acetyl,

X3=—H, —OH, —$CH_3$, O-acetyl

Surprisingly, the novel compounds are highly potent thrombin inhibitors. It is also surprising that the stability to intestine and liver homogenates and to trypsin and chymotrypsin is crucially improved compared with known compounds.

Surprisingly, it has also been found that the activity as well as the specificity of the compounds according to the invention is crucially influenced by the group R'. The compound with R'=β-naphthylsulfonyl and $R_1$=Asp has very similar activity in respect of inhibition of thrombin and of trypsin, that is to say a low specificity. It is possible by introducing alkyl groups and/or hydroxyalkyl groups and/or hydroxyl groups and/or carboxyl groups on the sulfonic acid residue R', which include, preferably, groups with up to 3 carbon atoms, particularly preferably methyl and/or methoxy groups, to achieve a significant increase in specificity for thrombin. This means that substitution by one or more groups of this type produces substances with properties showing, in particular and surprisingly, an enhanced inhibition of thrombin with, at the same time, less inhibition of trypsin.

It is thus possible to influence in a crucial manner the properties of the substances in this class of substances which are interesting as thrombin inhibitors by the derivatization patterns described here, which result in superior compounds.

Structures according to the invention which have particular activity, as is evident from the $K_i$ values, are those based on R'=phenyl and $R_1$=—$CH_2$—COOH (i.e. L-Asp) and the compounds derived therefrom where R' carries either alkyl groups which contain up to 4 carbon atoms, or else groups of the structure O—X in which O=oxygen and X= hydrogen, methyl, ethyl, n-propyl, i-propyl or tert.-butyl, or else a group of the structure —COOY in which Y=hydrogen, methyl, ethyl, n-propyl, i-propyl, tert.-butyl, i-butyl, i-pentyl or neo-pentyl.

In a narrower sense and without restriction to the following examples, suitable and preferred as R' are the following groups:

| | |
|---|---|
| 6,7-Dimethoxynaphthyl- | (β-Dmn) |
| 5-Methoxynaphthyl- | (β-Mns) |
| 2,2,5,7,8,-Pentamethylchroman- | (Pmc) |
| 5,6,7,8,-Tetrahydronaphthalene- | (Thn) |
| 5,6,7,8,-Tetramethylnaphthyl- | (Tmn) |
| Phenyl- | (Phl) |
| 4-Methoxy-2,3,6-trimethylphenyl- | (Mtr) |
| 2,3,4,5,6-Pentamethylphenyl- | (Pme) |
| 4-Methoxy-2,3,5,6-tetramethylphenyl- | (Mte) |
| 4-Hydroxy-2,3,6-trimethylphenyl- | (Htr) |
| 4-Carboxyphenyl- | (Cph). |

The Mtr group has very special activity in this connection, i.e. this takes the form of a structure derived from 4-methoxy-2,3,6-trimethylbenzenesulfonyl chloride.

Suitable as group C are alpha-, beta-, gamma- or delta-amino acids and derivatives thereof, and N-glycosidically linked uronic acid such as, for example, β-D-amino-glucuronic acid.

Surprisingly, the compounds according to the invention also have improved tolerability and are therefore superior to the compounds of the state of the art. Thus, for example, an $LD_{50}$ (rat, i.v.) of about 120 mg/kg was determined for the compound β-naphthylsulfonyl-L-Asp-D,L-Aph-Pip, whereas this value for NAPAP is about 20 mg/kg. It has also been found than another carboxyl group on the group R' further improves the tolerability of the compounds according to the invention.

The improved tolerability of the inhibitors, according to the invention, with acidic groups is manifested by a reduced histamine release and a reduced fall in blood pressure.

The fact that these compounds have, besides the potent antithrombin activity, specificity and more favorable tolerability, an improved stability to enzymes, for example to trypsin and chymotrypsin and liver and intestine homogenates, makes these substances a class of interesting anticoagulants.

Another advantage of the compounds according to the invention which should be mentioned is the oral bioavailability which makes these compounds so particularly attractive.

The compounds according to the invention can be used as antithrombotics for therapy to prevent the formation of blood clots, or in diagnosis.

The invention also relates to the provision of derivatives of these substances, especially ester compounds. These have the feature that the carboxyl group on the amino acid $R_1$ is esterified with aliphatic alcohols with up to 17 carbon atoms. Accordingly, esters of this type are derived from alcohols such as methyl, ethyl, isopropyl, n-propyl, n-butyl, isobutyl, tert.-butyl, n-pentyl, isopentyl, neo-pentyl, octyl, decyl, dodecyl, hexadexyl or heptadecyl alcohol. The derivatization with alcohols improves the lipid solubility of the substances according to the invention, which is reflected by favorable enteral absorbability.

If hydroxyl functionalities are present on the radicals $R_2$ and $R_3$ they can optionally be esterified with carboxylic acids. Examples of such carboxylic acids are acetic acid, succinic acid, pivalic acid, hexanecarboxylic acid, octanecarboxylic acid, decanecarboxylic acid, dodecanecarboxylic acid or hexadecanecarboxylic acid.

Since the amidino functionality is, by reason of the basic action, usually in salt form, the thrombin inhibitors according to the invention can also occur in different salt forms. The salt form moreover has a considerable effect on the solubility of the compounds and on the absorbability on therapeutic administration. Salt forms which may be mentioned here are formates, acetates, caproates, oleates or salts of carboxylic acids with up to 16 carbon atoms, chlorides, bromides, iodides, alkane-sulfonates with up to 10 carbon atoms, salts of dicarboxylic acids and tricarboxylic acids, such as citrates or tartrates.

The following are particularly preferred:

A compound of the formula I in which R' is β-naphthyl, $R_1$ is —$CH_2$—COOX with X equal to hydrogen and $R_2$ and $R_3$ together are piperidine.

A compound of the formula I in which R' is β-6,7-dimethoxynaphthyl, $R_1$ is —$CH_2$—COOX with X equal to hydrogen and $R_2$ and $R_3$ together are piperidine.

A compound of the formula I in which R' is β-tetralin, $R_1$ is —$CH_2$—COOX with X equal to hydrogen and $R_2$ and $R_3$ together are piperidine.

A compound of the formula I in which R' is 4-methoxy-2,3,6-trimethylphenyl, $R_1$ is —$CH_2$—COOX with X equal to hydrogen and $R_2$ and $R_3$ together are piperidine.

A compound of the formula I in which R' is 4-carboxyphenyl, $R_1$ is —$CH_2$—COOX with X equal to hydrogen and $R_2$ and $R_3$ together are piperidine.

A compound of the formula I in which R' is 4-hydroxy-2,3,6-trimethylphenyl, $R_1$ is —$CH_2$—COOX with X equal to hydrogen and $R_2$ and $R_3$ together are piperidine.

A compound of the formula I in which R' is 2,2,5,7,8-pentamethylchroman, $R_1$ is —$CH_2$—COOX with X equal to hydrogen and $R_2$ and $R_3$ together are piperidine.

A compound of the formula I in which X is an alcohol residue which has up to 17 carbon atoms.

A compound of the formula I where $R_1$ has the structure —$(CH_2)_n$—$SO_3H$ with n=1 to 4.

A compound of the formula I where $R_1$ has the structure —$(CH_2)_n$—$PO(OH)_2$ with n=1 to 4.

A compound of the formula I wherein $R_2$ and $R_3$ together are 3-hydroxymethylpiperidine.

A compound of the formula I wherein the hydroxyl functionality is esterified with a carboxylic acid which contains up to 17 carbon atoms.

The invention also relates to a process for the preparation of a compound of the formula I, which comprises coupling a protective acidic amino acid via the carboxyl group in the alpha position to the alpha-amino functionality of a p-cyanophenylalanine amide derivative, removing the N-alpha protective group, coupling a sulfonyl chloride to this nitrogen group, converting the cyano group into the amidino functionality and, where appropriate, eliminating a protective group which is present on the third functionality of the acidic amino acid.

It is necessary for the incorporation of the acidic amino acids, which include, in particular, the amino acids aspartic acid (Asp) or glutamic acid (Glu), to have recourse to the use of protected amino acids. It is obligatory in this connection to block the N-alpha functionality with a protective group. Protective groups which are preferably used for this are groups of the urethane type such as tert.-butyloxycarbonyl (Boc), benzyloxycarbonyl (Z or Cbo), biphenylisopropyloxycarbonyl (Bpoc), dimethoxydimethylbenzyloxycarbonyl (Ddz) or 9-fluorenylmethyloxycarbonyl (Fmoc). Particular attention must be directed in this connection at masking the carboxyl group in the side functionality.

Preferably employed for this purpose are esters which can be eliminated as required after the synthesis. If it is intended to eliminate the side-group masking after the synthesis, the tert.-butyl ester is preferably employed. It has been found that a suitable N-alpha protective group is, for example, the Fmoc group which can be eliminated with base or the very acid-labile Bpoc or Ddz group. If the side functionality in the acidic amino functionality in the final compound is to remain esterified, the corresponding N-alpha-Z-protected amino acid alpha tert.-butyl ester is preferably esterified with the required alcohol, the Z group is removed by hydrogenolysis, the appropriate sulfonyl chloride is reacted with the amino acid derivative, the tert.-butyl ester is eliminated by acidolysis and the isolated product is coupled to the amino functionality of the cyanophenylalanine derivative. The production of the sulfamide linkage is generally carried out by standard processes by coupling the appropriate sulfonyl chlorides to the amino group of the acidic amino acid. Compounds which contain a phenol group on R' are prepared via the corresponding protected phenol ethers, particularly preferably tert.-butyl ethers, which, after conversion into the sulfonyl chlorides and preparation of the sulfamide linkage, are eliminated by acidolysis and thus provide the required final compounds.

Free phenol groups can also be prepared by other known processes, for example using demethylating agents, particularly preferably boron tribromide in an organic solvent, and dichloromethane should be mentioned as preferred.

A second possibility is first to prepare the sulfamide linkage to the acidic amino acid and subsequently to condense the latter onto the para-cyanophenylalanine derivative. To prepare the arylsulfonylamino acid tert.-butyl esters or heteroarylsulfonylamino acid tert.-butyl esters, the corresponding sulfonyl chloride and the amino acid tert.-butyl ester alpha-methyl ester are reacted in dimethylformamide with the addition of base, for example N-methylmorpholine or diisopropylethylamine. The methyl ester is hydrolyzed with alkali, and the coupling to the Aph or cyanophenylalanine derivative is carried out by means of a carbodiimide reaction. It was possible to prepare the compounds according to the invention with a sulfonic acid group (B=SO$_3$H), preferably with cysteinesulfonic acid, using N-alpha-protected cysteinesulfonic acid. For this purpose, the Boc group is bonded to the nitrogen of the amino acid, and this compound is coupled to the cyanophenylalanine piperidide. After elimination of the protective group, the required sulfonyl chloride is reacted therewith. It is also suitable to prepare the corresponding cysteine compound with free sulfhydryl functionality and then to convert the latter with an oxidizing agent, for example with performic acid, into the sulfonic acid. Preferably used for this is Boc-Cys(SStBu) or Boc-Cys(Trt). The oxidation reactions are carried out after elimination of the sulfur protective groups.

Compounds according to the invention with a group C from the group of alpha-, beta-, gamma- or delta-amino acid are prepared by processes known per se. It is preferable to couple an N-protected acidic amino acid, for example aspartic acid, where the definitive sulfonamide structure is preferably introduced as protective group, to a carboxyl-protected amino acid. The alpha-carboxyl functionality is protected in this case, preferably as methyl ester. The coupling is preferably carried out with condensing agents of the carbodiimide type, preferably with dicyclohexylcarbodiimide. Hydroxybenzotriazole can be added to the reaction. Dimethylformamide is preferably used as solvent.

After isolation of the substances, the carboxyl group in the alpha position is deprotected, which is carried out by hydrolysis in the case of the methyl esters.

These precursors are then coupled, using the processes already described herein, to the amino functionality of the cyanophenylalanine, and reacted further, i.e. the amidino functionality is prepared. To prepare compounds according to the invention where the group C is an N-glycosidically linked uronic acid, firstly the N-alpha and C-alpha protective acidic amino acid is linked to the appropriately protected carbohydrate moiety. The preparation is carried out by processes known per se from the literature, such as, for example, A. Klemer et al.; J. Carbohydrate Chemistry, 7 (4), 785–797 (1988) or T. Takeda et al.; Carbohydrate Research, 207, 71–79 (1990) or L. Urge et al.; Tetrahedron Letters, 32 (9), 3445–3448 (1991) or R. Walczyna et al.; Carbohydrate Research; 180, 147–151 (1988). After elimination of the nitrogen protective group of the amino acid, a sulfonyl chloride is coupled on as described above, and the C-alpha carboxyl group is eliminated. This is followed by coupling to the amino group of the C-terminal portion, preferably using for this an amidinophenylalanineamide, particularly preferably D-4-amidinophenylalanine piperidide. After deprotection of the uronic acid, the substances are purified by conventional processes such as gel permeation chromatography or ion exchange chromatography.

To prepare the amidino functionality, the p-cyanophenylalanine compounds are dissolved in pyridine and triethylamine and saturated with hydrogen sulfide. After 2 to 3 days, the solution is stirred into dilute hydrochloric acid, and the precipitate is isolated. Methylation with a methylating agent, preferably methyl iodide, and reaction with an ammonium salt such as ammonium acetate in an alcohol, preferably methanol, result in the peptide derivative with amidino functionality. Treatment with trifluoroacetic acid or HCl in acetic acid for acidolysis results in the required product. The subsequent gel permeation chromatography on $^R$Sephadex LH-20 in methanol yields the pure substance. The final compounds are checked for identity by NMR and mass spectrometry and for purity by HPLC and thin-layer chromatography. Ion exchange chromatography is preferably used to convert into the required salt forms. This entails the appropriate compound being bound to a carboxymethylated ion exchanger resin, for example CM-$^R$Fractogel, and being eluted with the required acid. The final product is obtained in crystalline form by lyophilization. Other required salt forms can be obtained from the acetate salts.

The inhibitors according to the invention are tested to assess their activity according to various criteria, and these are preferably determination of the K$_i$, of the IC$_{50}$ and of the partial thromboplastin time (PTT) in vivo and in vitro. To test the specificity, the IC$_{50}$ values for various serine proteases, especially thrombin and trypsin, are determined. The stability of the substances according to the invention is determined by incubating a sample of the substance with a pure enzyme, preferably trypsin, chymotrypsin or papain or with liver or intestine homogenates, and taking samples from the solutions at intervals of time and measuring them, preferably by HPLC. It is possible to show in this way that the claimed compounds are more stable and are broken down less rapidly by comparison with the state of the art. The claimed compounds are specific and highly active thrombin inhibitors with a considerable antithrombotic potential which exceeds the previously disclosed low molecular weight inhibitors, and which in some cases are also distinguished by the possibility of enteral administration, as it was possible to show with the compound Mtr-L-Asp-D-Aph-Pip.

The invention also relates to a diagnostic or therapeutic agent containing a compound of the formula I.

The invention additionally relates to the use of a compound of the formula I in a process for the production of a diagnostic aid or of a pharmaceutical with antithrombotic action.

| Abbreviations: | |
|---|---|
| Aph | Amidinophenylalanine |
| NAPAP | β-Naphthylsulfonyl-glycyl-D,L-p-amidinophenylalanyl-piperidide |
| Asp | Aspartic acid |
| Asn | Asparagine |
| Glu | Glutamic acid |
| Cys(SO$_3$H) | Cysteinesulfonic acid |
| β-Dmn | 6,7-Dimethoxynaphthyl |
| β-Mns | 5-Methoxynaphthyl |
| Pmc | 2,2,5,7,8,-Pentamethylchroman |
| Thn | 5,6,7,8,-Tetrahydronaphthalene |
| Tmn | 5,6,7,8,-Tetramethylnaphthyl |
| Phl | Phenyl- |
| Mtr | 4-Methoxy-2,3,6-trimethylphenyl-4-methylphenyl |
| Pme | 2,3,4,5,6-Pentamethylphenyl- |
| Mte | 4-Methoxy-2,3,5,6-tetramethylphenyl- |
| Htr | 4-Hydroxy-2,3,6-trimethylphenyl- |
| Cph | 4-Carboxyphenyl- |
| Z (Cbo) | Benzyloxycarbonyl- |
| Boc | tert.-Butyloxycarbonyl |
| Bpoc | Biphenylisopropyloxycarbonyl- |
| Ddz | Dimethoxydimethylbenzyloxycarbonyl |
| Fmoc | Fluorenylmethyloxycarbonyl |
| Pip | Piperidine |
| OtBu | tert.-Butyl ester |
| OMe | Methyl ester |
| OEt | Ethyl ester |
| OiBu | iso-Butyl ester (sec-butyl ester) |
| OiPr | iso-Propyl ester |
| OnPe | neo-Pentyl ester |
| TLC | Thin-layer chromatography |
| DCCI | Dicyclohexylcarbodiimide |
| DMF | Dimethylformamide |
| FAB-MS | Fast atom bombardment mass spectrometry |
| DIPEA | Diisopropylethylamine |
| HOBt | Hydroxybenzotriazole |

The following examples describe the invention in more detail:

Beta-Naphthylsulfonyl-L-aspartic Acid
D-p-amidinophenyl-alanyl-piperidide

1. Boc-D-p-cyanophenylalanyl-piperidide 50 g (255 mmol) of p-cyanobenzyl bromide, 55 g (255 mmol) of diethyl acetamidomalonate and 2 g of potassium iodide in 250 ml of absolute dioxane were heated to boiling. To this was added dropwise over the course of 3 hours a freshly prepared solution of 6 g (260 mmol) of sodium in ethanol. After refluxing for a further 3 hours, the mixture was cooled to 80 degrees and, over the course of 3 hours, 170 ml of 3N sodium hydroxide solution were added. The mixture was heated at 95 degrees for 4 hours. After cooling, the pH was adjusted to 1 with 6N HCl, and the dioxane was evaporated off. Any precipitate which separated out was removed by filtration. The pH was adjusted to 9 with sodium hydroxide solution, and 2 extractions with ethyl acetate were carried out. The aqueous phase was again adjusted to pH 1 with hydrochloric acid, whereupon N-acetyl-cyanophenylalanine crystallized out. The crystals were collected, washed several times with water and dried under high vacuum.

Yield: 47 g (79.2 % of theory)

Purity check: TLC Rf=0.5 (chloroform 50/methanol 10/glacial acetic acid 2.5//parts by volume)

24 g of this product were dissolved in 3 liters of water by addition of 3N sodium hydroxide solution, and the pH was adjusted to 6–6.5. To this were added 500 mg of acylase, and the mixture was incubated at 37 degrees for 4 days. After this, the solution was subjected to ultrafiltration to remove the acylase and was then concentrated to a volume of 1 liter. Adjustment to pH 1 was followed by extraction several times with ethyl acetate. The organic phase was washed with a little concentrated brine and dried over sodium sulfate, and the solvent was evaporated off. 8.2 g of N-acetyl-D-cyanophenylalanine (68% of theory) were obtained. 22 ml of glacial acetic acid and 4.3 ml of concentrated hydrochloric acid with 40 ml of water were added to 8 g of this compound, and the mixture was heated to boiling for 24 hours. The elimination solution was evaporated and adherent traces of acid were entrained out with methanol, and then reprecipitation was carried out with methanol/diethyl ether.

Yield: 6.6 g (85% of theory)

5 g of D-cyanophenylalanine hydrochloride were dissolved in 14 ml of water with the addition of 7.5 ml if diisopropylethylamine. To this was added a solution of 6 g of tert.-butyloxycarbonyl-oxyimino-2-phenylacetonitrile in 17 ml of dioxane, and the mixture was stirred overnight. 40 ml of water and 50 ml of ethyl acetate were added. The aqueous phase was separated off, and the organic phase was extracted once more with 1M potassium bicarbonate. The combined aqueous phases were washed once more with 10 ml of diethyl ether and subsequently adjusted to pH 3 with hydrochloric acid. 3 extractions with ethyl acetate were carried out, and the organic phase was washed with sodium chloride solution and dried over sodium sulfate. Removal of the solvent by evaporation resulted in 5.6 g (78%) of Boc-D-cyanophenylalanine. 3.26 g (10 mmol) of Boc-D-cyanophenylalanine, 1.49 g (11 mmol) of HOBt and 2.42 g (12 mmol) of DCCI were dissolved in 50 ml of DMF and stirred for 1 hour. 1 ml of piperidine was added, and the mixture was stirred overnight. Precipitated dicyclohexylurea was removed by filtration, the DMF was removed by distillation, and the residue was taken up in ethyl acetate. Washing was carried out 3 times with potassium bicarbonate, 3 times with 1M potassium bisulfate and 3 times with saturated brine. Drying of the organic phase with sodium sulfate and removal of the solvent by distillation resulted in 3.16 g (80%) of Boc-D-cyanophenylalanyl piperidide Purity check: TLC Rf=0.27 (chloroform)

2. D-Cyanophenylalanyl-piperidine hydrochloride 3 g of the Boc-protected compound were dissolved in 50 ml of 1.2N HCl in glacial acetic acid and stirred at room temperature for 30 min. The elimination reagent was removed by distillation in vacuo and then entrained out with toluene, and the residue was triturated with a little diethyl ether. The crystals were collected and dried in vacuo.

Yield: 2.2 g (90% of theory)

3. Ddz-Asp(tBu)-D-cyanophenylalanyl piperidide 2.88 g (7 mmol) of Ddz-Asp(tBu), 1.04 g of HOBt, 1.73 g of DCCI and 2.06 g (7 mmol) of cyanophenylalanyl piperidide hydrochloride were dissolved in 50 ml of DMF. Addition of 2.4 ml (14 mmol) of diisopropylethylamine was followed by stirring at room temperature in the dark for 1 day. The solvent was removed by distillation in vacuo, the residue was taken up in ethyl acetate and washed 3 times with 1M potassium bisulfate solution, 3 times with potassium bicarbonate solution and 2 times with concentrated brine. The organic phase was dried over sodium sulfate, and the solvent was evaporated off. The residue was triturated with diisopropyl ether, and the crystals were collected and dried. 3.86 g (85% of theory) of Ddz-Asp(tBu)-D-cyanophenylalanyl piperidide were obtained.

4. β-Naphthylsulfonyl-Asp(tBu)-D-cyanophenylalanyl piperidide 3.25 g (5 mmol) of Ddz-Asp(tBu)-D-cyanophenylalanyl piperidide were dissolved in 200 ml of 5% strength trifluoroacetic acid in dichloromethane and stirred at room temperature for 30 min. The mixture was poured into 2M sodium bicarbonate solution, and the organic phase was washed twice with sodium bicarbonate solution and once with concentrated brine. After drying over sodium sulfate, the solvent was evaporated off and the oily residue was extracted three times with diisopropyl ether. The oily residue was dissolved in dichloromethane with the addition of 1.71 ml (10 mmol) of DIPEA, and 1.13 g (5 mmol) of β-naphthylsulfonyl chloride were added to this with stirring. The mixture was stirred at room temperature overnight and then the organic phase was washed 3 times each with NaHCO$_3$ solution, potassium bisulfate solution and sodium chloride solution. The organic phase was dried over sodium sulfate and then the solvent was removed by distillation, and the resulting substance was used without purification for the subsequent reaction.

5. β-Naphthylsulfonyl-Asp(tBu)-D-amidinophenylalanyl piperidide

The compound obtained in 4. was dissolved in 30 ml of dry pyridine and, after addition of 1 ml of triethylamine, gaseous hydrogen sulfide was passed in for 3 hours. The mixture was left to stand at room temperature for three days and then poured into a mixture of 100 g of ice and 50 ml of concentrated hydrochloric acid. The precipitate was filtered off with suction and washed with water. The thioamide was dried and then taken up in 50 ml of acetone, and 1.5 ml of methyl iodide were added. The mixture was boiled under reflux for 30 minutes. After cooling, precipitation was induced with diethyl ether. The precipitate was dissolved in dichloromethane and washed twice with water. The organic phase was dried over sodium sulfate and the solvent was removed, and then the residue was taken up in 30 ml of dry methanol, and 200 mg of ammonium acetate were added. The mixture was heated at 60 degrees for 3 hours. The solvent was evaporated off in vacuo. The product was subjected to purification by chromatography on Sephadex LH-20 in methanol.

Yield: 630 mg

Purity check: TLC: Rf=0.55 (chloroform 50/methanol 10/glacial acetic acid 2.5//volumes)

FAB-MS: M+H 636

6. β-Naphthylsulfonyl-Asp-D-amidino-phenylalanyl piperidide 500 mg of the substance isolated in 5. were dissolved in 5 ml of 1.2N HCl in glacial acetic acid and stirred at room temperature for 1 hour. The solvent was evaporated off and then the residue was triturated with diethyl ether and collected on a filter frit. The product was dried over phosphorus pentoxide under high vacuum. The crude substance was dissolved in water and bound to CM-Fractogel ion exchanger. Elution was carried out with 5% strength acetic acid. Lyophilization resulted in 290 mg of the acetate salt. The correct structure was confirmed by $^{13}$C-NMR spectroscopy.

FAB-MS: M+H 580

6,7-Dimethoxy-β-naphthalenesulfonyl-L-Asp-D-p-amidinophenylalanyl Piperidide

The preparation was carried out in analogy to the above example. 6,7-Dimethoxy-β-naphthalenesulfonyl chloride was employed in place of β-naphthalenesulfonyl chloride.

FAB-MS: M+H 640

5,6,7,8-Tetrahydro-β-naphthalenesulfonyl-L-Asp-D-p-amidinophenylalanyl Piperidide 5,6,7,8-Tetrahydro-β-naphthalenesulfonyl-L-Asp-D-p-amidinophenylalanyl piperidide was prepared using 5,6,7,8-tetrahydro-β-naphthalenesulfonyl chloride and the above process.

FAB-MS: M+H 584

4-Methoxy-2,3,6-trimethylphenylsulfonyl-L-Asp-D-p-amidinophenylalanyl Piperidide 4-Methoxy-2,3,6-trimethylphenylsulfonyl-L-Asp-D-p-amidinophenylalanyl piperidide was prepared using 4-methoxy- 2,3,6-trimethylphenylsulfonyl chloride and the above process.

FAB-MS: M+H 602

4-Methoxy-2,3,6-trimethylphenylsulfonyl-L-Cys(SO$_3$H)-D-p-amidinophenylalanyl Piperidide 4-Methoxy-2,3,6-trimethylphenylsulfonyl-L-Cys(SO$_3$H)-D-p-amidinophenylalanyl piperidide was prepared using 4-methoxy- 2,3,6-trimethylphenylsulfonyl chloride and the above process.

FAB-MS: M+H 638

4-Methoxy-2,3,6-trimethylphenylsulfonyl-L-asparaginyl-N-[β-D-glucopyranosyl)uronic acid]-D-p-amidinophenylalanyl Piperidide (Mtr-L-Asp (β-D-aminoglucuronic acid)-D-Aph-pip)

1. Methyl (2,3,4-tri-O-acetyl-β-D-glucopyranosylamine)uronate 2 g of methyl (2,3,4-tri-O-acetyl-β-D-glucopyranosyl azide)uronate were dissolved in 200 ml of ethyl acetate/methanol (2:1;V:V), 2 g of palladium/charcoal were added, adjusted to pH 7.5 with triethylamine and treated with hydrogen flowing through for one hour. The reaction mixture was filtered and the solvent was evaporated off.

Yield: 1.9 g

Purity check: TLC Rf=0.35 (dichloromethane:acetone/2:1)

2. 2-N-(Z)-4-N-[Methyl (2,3,4-tri-O-acetyl-β-D-glucopyranosyl] uronate]-L-asparagine tert.butyl ester 1.26 g of Z-aspartic acid alpha-tert.-butyl ester, 0.9 g of HOBt and 1.4 g of dicyclohexylcarbodiimide were dissolved in 100 ml of THF and, at 0° C., 1.4 g of stage 1 were added. The mixture was stirred at room temperature overnight, and the solvent was evaporated off in vacuo. The residue was taken up in chloroform, washed with water and dried with sodium sulfate, and the solvent was distilled off. The residue was purified on silica gel using chloroform/acetone (6:1/V:V).

Yield: 1.7 g

Purity check: TLC Rf=0.72 (chloroform:acetone/6:1)

3. 4-N-[Methyl (2,3,4-tri-O-acetyl-β-D-glucopyranosyl)uronate] -L-asparagine tert.butyl ester 0.9 g of the second stage was dissolved in 20 ml of methanol, a spatula tip of palladium/charcoal was added, and the mixture was hydrogenated for 5 hours. The catalyst was removed by filtration and then the solvent was removed by distillation, and the residue (0.75 g) was employed without further purification for the next reaction.

4. 2-N-(4-Methoxy-2,3,6-trimethylbenzenesulfonyl)-4-

N-[ methyl (2,3,4-tri-O-acetyl-β-D-glucopyranosyl)uronate]-L-asparagine tert.butyl ester 1.73 g of the preceding stage, 1.2 ml of diisopropylethylamine and 0.8 g of Mtr chloride were dissolved in 80 ml of DMF and stirred at room temperature overnight. The solvent was evaporated off in vacuo, and the residue was taken up in ethyl acetate and washed three times with water. The organic phase was dried with sodium sulfate and evaporated in vacuo. Further purification was carried out by chromatography on silica gel with dichloromethane/acetone (3:1/V:V).

Yield: 1.57 g

Purity check: TLC Rf=0.87 (dichloromethane:methanol/10:1)

5. 2-N-(4-Methoxy-2,3,6-trimethylbenzenesulfonyl)-4-N-[ methyl (2,3,4-tri-O-acetyl-β-D-glucopyranosyl)uronate]-L-asparagine 2.2 g of the fourth stage were dissolved in 50 ml of trifluoroacetic acid/dichloromethane (1:1/V:V) and stirred at room temperature for I hour. The acidic mixture was distilled off in vacuo and adherent traces of acid were evaporated off using toluene in vacuo. The resulting product was used without further purification for the next reaction.

Yield: 1.2 g

Purity check: TLC Rf=0.7 (chloroform:methanol/3:1)

6. 2-N-(4-Methoxy-2,3,6-trimethylbenzenesulfonyl )-4-N-[methyl (2,3,4-tri-O-acetyl-β-D-glucopyranosyl)uronate]-L-asparaginyl-D-4-amidinophenylalanine piperidide 1.0 g from the preceding stage, 0.23 g of HOBt and 0.37 g of DCCI were dissolved in 50 ml of DMF and stirred at 4° C. for 30 minutes. Then 0.4 g of D-4-amidinophenylalaninepiperidide and 0.5 ml of N-methylmorpholine were added. The mixture was stirred at room temperature overnight and filtered, and the solvent was evaporated off in vacuo. The crude product was chromatographed on silica gel with chloroform/methanol 5:1.

Yield: 1.2 g

Purity check: TLC Rf=0.7 (chloroform/methanol/3:1)

7. 2-N-(4-Methoxy-2,3,6-trimethylbenzenesulfonyl)-4-N-[methyl (β-D-glucopyranosyl)uronate]-L-asparaginyl-D-4-amidinophenylalanine piperidide 1.1 g of the preceding stage were dissolved in 50 ml of methanol and adjusted to pH 9 with 1N sodium hydroxide solution. After 2 hours at pH 8.5–9, the mixture was neutralized with methanolic HCl and the solvent was evaporated off in vacuo. The residue was chromatographed on Sephadex$^R$ LH-20 in methanol.

Yield: 0.9 g

Purity check: TLC Rf=0.34 (chloroform:methanol:water/40:20:1)

8. 2-N-(4-Methoxy-2,3,6-trimethylbenzenesulfonyl)-4-N-[(β-D-glucopyranosyl)uronate]-L-asparaginyl-D-4-amidinophenylalanine piperidide 0.9 g of the last stage was taken up in 100 ml of chloroform:methanol:water (40:20:1/V:V:V) and 0.2 g of barium hydroxide was added. The mixture was stirred at room temperature for 3 hours adjusted to pH 3.5 with HCl in methanol, and the solvent was evaporated off. The residue was chromatographed on Sephadex$^R$ LH-20 in methanol.

Yield: 0.72 g

Purity check: TLC Rf=0.32 (chloroform:methanol:water/8:6:1)

FAB-MS: 777

4-Methoxy-2,3,6-trimethylbenzenesulfonyl-L-aspartic Acid (Gamma-aminobutyric Acid)-D-Aph-piperidide 1. 4-Methoxy-2,3,6-trimethylbenzenesulfonyl-L-aspartic acid (tert.-butyl gamma-aminobutyrate)-D-cyanophenylalanine piperidide 1 g of Mtr-Asp-D-cyanophenylalanine piperidide was dissolved in 30 ml of DMF, and 0.34 ml of diisopropylethylamine, 0.39 g of HOBt, 0.42 g of tert.-butyl gamma-aminobutyrate and 0.66 g of dicyclohexylcarbodiimide were added. The mixture was stirred initially in an ice bath for one hour and then at room temperature overnight. The precipitated dicyclohexylurea was filtered off and the solvent was evaporated off in vacuo. The oily residue was taken up in ethyl acetate and washed twice each with water, 1M potassium bicarbonate solution, 1M potassium bisulfate solution and saturated brine. After drying over sodium sulfate, the solvent was removed by distillation.

Yield: 1.1 g

Purity check: TLC Rf=0.89 (chloroform:methanol/9:1)

2. 4-Methoxy-2,3,6-trimethylbenzenesulfonyl-L-aspartic acid (tert.-butyl gamma-aminobutyrate)-D-Aph-piperidide The cyano group was converted into the amidino group as in the fifth stage of the first example.

Yield: 500 mg

Purity check: TLC Rf=0.4 (chloroform:methanol:acetic acid/50:10:2.5)

3. 4-Methoxy-2,3,6-trimethylbenzenesulfonyl-L-aspartic acid gamma-aminobutyric acid)-D-Aph-piperidide 400 mg of the preceding stage were taken up in 15 ml of 1.2N HCl/acetic acid and stirred at room temperature for 90 minutes. The acid mixture was removed by distillation and twice mixed with toluene and the toluene evaporated off. The crude product was dissolved in 3 ml of methanol and crystallized by dropwise addition to 50 ml of diethyl ether. The precipitate was collected and dried in vacuo.

Yield: 320 mg

Purity check: TLC Rf=0.25 (chloroform:methanol:acetic acid/50:10:2.5)

FAB-MS: 686

Omitting the racemate resolution by means of acylase in Step 1., the corresponding racemic D,L-cyanophenylalanine piperidides were likewise converted into the compounds according to the invention, which are likewise highly potent thrombin inhibitors.

TABLE I

Compilation of Compounds* According to the Invention

*The salt forms on the amidino functionality are not specified

β-Naphthylsulfonyl-L-Glu-D-Aph-Pip
β-Naphthylsulfonyl-L-Asp-D-Aph-Pip
β-Naphthylsulfonyl-D-Asp-D,L-Aph-Pip
β-Naphthylsulfonyl-L-Asp-D,L-Aph-Pip
β-Naphthylsulfonyl-L-Asp-D,L-Aph-3-hydroxymethylpiperidide
β-Naphthylsulfonyl-L-Asp(OtBu)-D-Aph-Pip
β-Naphthylsulfonyl-L-Asp(OMe)-D-Aph-Pip
β-Naphthylsulfonyl-L-Asp(OEt)-D-Aph-Pip
β-Naphthylsulfonyl-L-Asp(OiBu)-D-Aph-Pip
Mtr-D-Asp-D,L-Aph-Pip
Mtr-L-Asp(OtBu)-D-Aph-Pip
Mtr-L-Asp(OMe)-D-Aph-Pip Mtr-L-Asp(OEt)-D-Aph-Pip
Mtr-L-Asp(OiBu)-D-Aph-Pip
Mtr-L-Asp(OiPr)-D-Aph-Pip
Mtr-L-Asp-D-Aph-Pip
Mte-L-Asp-D-Aph-Pip
Mte-L-Asp(OiBu)-D,L-Aph-Pip
Htr-L-Asp(OtBu)-D-Aph-Pip
Htr-L-Asp-D-Aph-Pip
Mtr-L-Glu-D,L-Aph-Pip
Mtr-L-Asn-D-Aph-Pip
Mtr-D-Asn-D,L-Aph-Pip
Thn-L-Asn-D-Aph-Pip
Pme-L-Asp(OtBu)-D-Aph-Pip
Pme-L-Asp-D-Aph-Pip
Pme-L-Asp(OtBu)-D,L-Aph-Pip
Phl-L-Asp(OtBu)-D-Aph-Pip
Phl-L-Asp-D-Aph-Pip
β-Dmn-L-Asp(OtBu)-D-Aph-Pip
β-Dmn-L-Asp-D-Aph-Pip
Tos-L-Asp(OtBu)-D-Aph-Pip
Tos-L-Asp-D-Aph-Pip
Pmc-L-Asp(OtBu)-D-Aph-Pip
Pmc-L-Asp-D-Aph-Pip
β-Mns-L-Asp(OnPe)-D-Aph-Pip
β-Mns-L-Asp-D-Aph-Pip
Cph-L-Asp(OtBu)-D,L-Aph-Pip
Cph-L-Asp-D,L-Aph-Pip
Phl-L-Cys(SO₃H)-D-Aph-Pip
Mtr-L-Cys(SO₃H)-D,L-Aph-Pip
Mtr-L-Cys(SO₃H)-D-Aph-Pip
Mtr-L-Asp(gamma-aminobutyric acid)-D-Aph-Pip
Mtr-L-Asp(L-threonine)-D-Aph-Pip
Mtr-L-Asp(L-phenylalanine)-Aph-Pip
Mtr-L-Asn[(β-D-glucopyranosyl)uronate]-D-Aph-Pip

Determination of the Inhibition Constants for Thrombin

The inhibition constants ($K_i$) for the substances were determined by known enzyme kinetic methods. The purity of the human thrombin employed was determined to be 87% by means of active site titration. The assay solution for the $K_i$ determination was composed of buffer (50 mM tris-HCl, 75 mM NaCl, pH 7.8, 37 degrees C.), 100 pM thrombin, 0.1 mM substrate S2238 (Kabi) and inhibitor which covered a range from 0 to 0.2 μM. Inhibitor and enzyme were preincubated for 10 minutes, and the reaction was started by adding the chromogenic substrate S2238. The kinetics were evaluated using the mathematical algorithm for tight binding, which, with the aid of non-linear regression, yielded $K_i$ values (Table II) and the type of inhibition. The type of inhibition was found to be more than 90% competitive for all the inhibitors.

Determination of the Specificity of the Inhibitors

The specificity of the inhibitors for thrombin and trypsin was determined. The specificity is defined as the ratio of the $K_i$ values for trypsin and thrombin (Table II). The concentration of inhibitor which brought about 50% inhibition of enzyme activity was called the $IC_{50}$ (100% corresponds to the non-inhibited enzyme). The $IC_{50}$ for trypsin was determined as follows: Trypsin from bovine pancreas was preincubated with increasing concentrations of inhibitor in 25 mM tris-HCl, 10 mM $CaCl_2$, pH 7.8 at 37 degrees C. for 10 min. The enzymatic reaction was started by adding the substrate Chromozym TRY ($7.1 \times 10^{-5}$M). The liberation of pNA was measured at 405 nm after one hour. The $IC_{50}$ values for thrombin were determined in an analogous manner, with the exceptions that human thrombin, buffer (50 mM tris-HCl, 50 mM NaCl, pH 7.8) and $5 \times 10^{-5}$M S 2238 were used. The $K_i$ values were calculated ($K_i = IC_{50}/S + KM$) from the $IC_{50}$ value for thrombin and trypsin. The specificities emerged from the ratio of the trypsin and thrombin values. The results are compiled in Table II.

TABLE II

Activities of some selected compounds

| | Compound | Specificity thrombin/trypsin | Thrombin inhibition $K_i$ (nanomol/l) |
|---|---|---|---|
| 1. | Napap | 24 | 11 |
| 2. | Nas-Asp-D-Aph-Pip | 7 | 10 |
| 3. | Dmn-Asp-D-Aph-Pip | 230 | 6 |
| 4. | Mtr-Asp-D-Aph-Pip | 125 | 1.5 |
| 5. | Mtr-Asp(tBu)-Aph-Pip | 297 | 0.9 |
| 6. | Mtr-Asp(iPr)-Aph-Pip | 378 | 0.6 |
| 7. | Nas-Asn-Aph-Pip | 48 | 6 |
| 8. | Mtr-Asn[(β-glucopyranosyl)uronate]-D-Aph-Pip | 4106 | 0.085 |
| 9. | Mtr-L-Cys (SO₃H)-D-Aph-Pip | 150 | 0.6 |
| 10. | Mtr-l-Asp(gamma-aminobutyric acid)-D-Aph-Pip | 1810 | 0.8 |

We claim:
1. A compound of the formula I

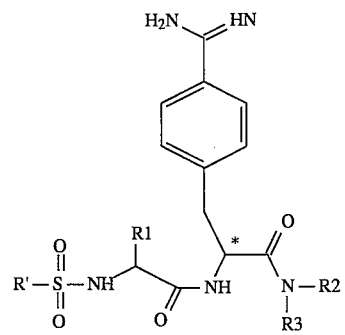

in which

R¹ is a naphthalene ring which is bonded in the alpha or beta position and is optionally substituted with up to 5 alkyl groups which contain up to 3 carbon atoms, and/or up to 5 alkoxy groups each with up to 3 carbon atoms, or is a tetralin ring or indane ring which is bonded in the alpha or beta position and is optionally substituted with up to 5 alkyl groups which are composed of up to 3 carbon atoms, and/or up to 5 alkoxy groups each with up to 3 carbon atoms, or is a phenyl ring which is optionally with up to 5 alkyl groups which contain up to 4 carbon atoms, and/or with up to three groups of the structure O—X in which 0 is oxygen and X is hydrogen, methyl, ethyl, n-propyl, i-propyl, tert.-butyl, i-butyl, i-pentyl or neo-pentyl, or is a chroman system which is optionally substituted with up to 5 alkyl groups which contain up to 3 carbon atoms, $R_1$ is a group of the structure A—B with A=—$(CH_2)_n$— and n=1–4 and B is selected from carboxyl, $C_1$–$C_{17}$ alkoxycarbonyl, carboxamide, sulfonic acid, an acid of phosphorous, boronic acid and tetrazole group, or $R_1$ is a group of the structure A—B—R— where A has the above meaning, B is carbonyl or sulfonyl, and the group R is an N-bonded naturally-occurring amino acid or gamma-butyric acid, optionally in esterified form, or R is a structure

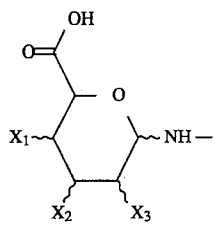

wherein X1, X2 and X3 are identical or different and are hydrogen, hydroxyl, methyl or O-acetyl, and $R_2$ and $R_3$ can be identical or different and are alkyl groups with up to 4 carbon atoms or together form a heterocyclic ring selected from pyrrolidine, piperidine, or azacycloheptane which can be optionally substituted with a hydroxyl group or a hydroxyalkyl group with up to 3 carbon atoms, and this hydroxyl group is optionally in esterified form, the corresponding acids being carboxylic acids which contain up to 17 carbon atoms, and in which the carbon atom marked with * is in the R or S configuration.

2. A compound as claimed in claim 1, wherein the carbon atom identified by * is in the R structure.

3. A compound as claimed in claim 1, in which R' is β-naphtyl, $R_1$ is —$CH_2$—COOX with X equal to hydrogen and $R_2$ and $R_3$ together are piperidine.

4. A compound as claimed in claim 1, in which R' is β-6,7-dimethoxynaphtyl, $R_1$ is —$CH_2$—COOX with X equal to hydrogen and $R_2$ and R3 together are piperidine.

5. A compound as claimed in claim 1, in which R' is β-tetralin, $R_1$ is —$CH_2$—COOX with X equal to hydrogen and $R_2$ and $R_3$ together are piperidine.

6. A compound as claimed in claim 1, in which R' is 4-methoxy- 2,3,6-trimethylphenyl, $R_1$ is —$CH_2$—COOX with X equal to hydrogen and $R_2$ and $R_3$ together are piperidine.

7. A compound as claimed in claim 1, in which R' is 4-carboxyphenyl, $R_1$ is —$CH_2$—COOX with X equal to hydrogen and $R_2$ and $R_3$ together are piperidine.

8. A compound as claimed in claim 1, in which R' is 4-hydroxy- 2,3,6-trimethylphenyl, $R_1$ is —$CH_2$—COOX with X equal to hydrogen and $R_2$ and $R_3$ together are piperidine.

9. A compound as claimed in claim 1, in which R' is 2,2,5,7,8-pentamethylchroman, $R_1$ is —$CH_2$—COOX with X equal to hydrogen and $R_2$ and $R_3$ together are piperidine.

10. A compound as claimed in claim 1, wherein X is an alcohol residue which has up to 17 carbon atoms.

11. A compound as claimed in claim 1, where $R_1$ has the structure —$(CH_2)_n$—$SO_3H$ with n=1 to 4.

12. A compound as claimed in claim 1, where $R_1$ has the structure —$(CH_2)_n$—$PO(OH)_2$ with n=1 to 4.

13. A compound as claimed in claim 1, wherein $R_2$ and $R_3$ together are 3-hydroxymethylpiperidine.

14. A compound as claimed in claim 13, wherein the hydroxyl functionality is esterified with a carboxylic acid which contains up to 17 carbon atoms.

* * * * *

UNITED STATES PATENT AND TRADEMARK OFFICE
CERTIFICATE OF CORRECTION

PATENT NO. : 5,457,114

DATED : October 10, 1995

INVENTOR(S) : Werner STÜBER et al.

It is certified that error appears in the above-indentified patent and that said Letters Patent is hereby corrected as shown below:

Title page, Abstract [57], and column 2, lines 30-40, formula (I),

" 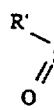 " should read -- 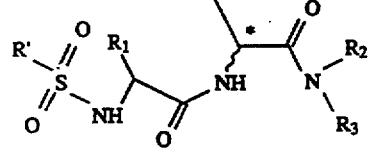 --.

Claim 1, column 16, formula I,

" 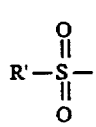 " should read -- 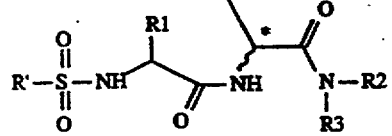 --.

UNITED STATES PATENT AND TRADEMARK OFFICE
CERTIFICATE OF CORRECTION

PATENT NO. : 5,457,114
DATED : October 10, 1995
INVENTOR(S) : Werner STÜBER et al.

It is certified that error appears in the above-indentified patent and that said Letters Patent is hereby corrected as shown below:

Claim 1, column 16, line 57, "0" should read --O--.

Claim 4, column 18, line 1, "R3" should read --$R_3$--.

Claim 6, column 18, line 6,
"4-methoxy- 2,3,6-trimethylphenyl"
should read --4-methoxy-2,3,6-trimethylphenyl--.

Claim 8, column 18, line 14,
"4-hydroxy- 2,3,6-trimethylphenyl"
should read --4-hydroxy-2,3,6-trimethylphenyl--.

Signed and Sealed this

First Day of October, 1996

Attest:

BRUCE LEHMAN

Attesting Officer    Commissioner of Patents and Trademarks